(12) United States Patent
Solis Herrera

(10) Patent No.: US 9,918,996 B2
(45) Date of Patent: Mar. 20, 2018

(54) METHODS OF USING QIAPINE

(71) Applicant: Arturo Solis Herrera, Aguascalientes (MX)

(72) Inventor: Arturo Solis Herrera, Aguascalientes (MX)

( * ) Notice: Subject to any disclaimer, the term of this patent is extended or adjusted under 35 U.S.C. 154(b) by 0 days.

(21) Appl. No.: 15/492,524

(22) Filed: Apr. 20, 2017

(65) Prior Publication Data

US 2017/0232009 A1    Aug. 17, 2017

Related U.S. Application Data

(62) Division of application No. 14/531,538, filed on Nov. 3, 2014, now Pat. No. 9,668,969, which is a division of application No. 13/401,892, filed on Feb. 22, 2012, now abandoned.

(51) Int. Cl.
| | |
|---|---|
| *A61K 31/60* | (2006.01) |
| *A61K 31/465* | (2006.01) |
| *A61K 9/08* | (2006.01) |
| *A61K 9/00* | (2006.01) |
| *A61K 31/4439* | (2006.01) |

(52) U.S. Cl.
CPC .............. *A61K 31/60* (2013.01); *A61K 9/006* (2013.01); *A61K 31/4439* (2013.01); *A61K 31/465* (2013.01)

(58) Field of Classification Search
None
See application file for complete search history.

(56) References Cited

U.S. PATENT DOCUMENTS

| | | | |
|---|---|---|---|
| 6,365,201 | B1 | 4/2002 | Wambebe et al. |
| 2002/0016344 | A1 | 2/2002 | Tracey |
| 2004/0248991 | A1 | 12/2004 | Fujii et al. |
| 2005/0282906 | A1 | 12/2005 | Tracey et al. |
| 2006/0051814 | A1 | 3/2006 | Jackowski et al. |
| 2007/0190114 | A1 | 8/2007 | Smart |
| 2009/0197921 | A1 | 8/2009 | Solis Herrera |

FOREIGN PATENT DOCUMENTS

| | | |
|---|---|---|
| AU | 2006343439 B2 | 5/2013 |
| EP | 1192277 A2 | 4/2002 |
| EP | 1328271 A2 | 7/2003 |
| EP | 1900850 A1 | 3/2008 |
| EP | 2027860 A1 | 2/2009 |
| EP | 2336128 A1 | 6/2011 |
| WO | 0189526 A1 | 11/2001 |
| WO | 03055486 A1 | 7/2003 |
| WO | 2006002375 A2 | 1/2006 |
| WO | 2007027910 A2 | 3/2007 |

OTHER PUBLICATIONS

Siems et al. "Elevated Serum Concentration of Cardiotoxic Lipid Peroxidation Products in Chronic Renal Failure in Relation to Severity of Renal Anemia". Clin Nephrol. Jul. 2002; 58 Suppl. 1:S20-S25 [Abstract Only].*
Galle J. "Oxidative Stress in Chronic Renal Failure". Nephrol Dial Transplant. 2001; 16:2135-2137.*
Kao et al. "Oxidative Stress in Renal Dysfunction: Mechanisms, Clinical Sequelae and Therapeutic Options". Journal of Human Hypertension. 2010; 24:1-8.*
Ceballos-Picot et al. "Glutathione Antioxidant System as a Marker of Oxidative Stress in Chronic Renal Failure". Free Radical Biology & Medicine. 1996; 21(6):845-853.*
Luciak M. "Antioxidants in the Treatment of Patients with Renal Failure". Rocz Akad Med Bialymst. 2004; 49:157-161.*
Priya et al. "Antioxidant Vitamins in Chronic Renal Failure". Biomedical Research, 2009; 20(1):67-70.*
Emerit et al, "Neurodegenerative Diseases and Oxidative Stress," Biomedicine and Pharmacotherapy, vol. 58, pp. 39-46 (2004).
Durner et al, "Salicylic Acid is a Modulator of Tobacco and Mammalian Catalases," J Bioi Chem., vol. 271, pp. 28492-28501 (1996).
Guan et al, "Dual Effects of Nicotine on Oxidative Stress and Neuroprotection in PC12 Cells," Neurochemistry International, vol. 43, pp. 243-249 (2003).
STN Registry No. 54-11-5. "Nicotine". STN Registry File. Retrieved May 28, 2014. Two Pages.
STN Registry No. 69-72-7. "Salicylic Acid". STN Registry File. Retrieved May 28, 2014. Two Pages.
Arias-Esparza et al. "The Unexpected Capability of Melanin to Split the Water Molecule and the Alzheimer's Disease". Neuroscience & Medicine. 2011; 2:217-221.
Aliev et al. Abstract 07. Journal of Nutrition, Health and Aging (Third Conference Clinical Trials on Alzheimer's Disease). Nov. 3-5, 2010; 14(2):S7.
Solis Herrera et al. "Human Photosynthesis and Central Nervous System Diseases". Journal of Neurological Sciences (Turkish). 2012; 29(3):654-668.
Human Photosynthesis [Online]. "Human Photosynthesis, a Conceptual Revolution of Biblical Proportions". [Retrieved May 28, 2014]. Retrieved from the Internet: <URL: http://humanphotosynthesis.com/index.html>. Published 2007.
Dictionary.com. [Online]. "Prophylactic". [Retrieved May 28, 2014]. Retrieved from the Internet: <URL: http://dictionary.reference.com/browse/prophylactic?s=t>.
Dictionary.com. [Online]. "Treat". [Retrieved May 28, 2014]. Retrieved from the Internet: <URL: http://dictionary.reference.com/browse/treat?s=t>.
Wang, et al., "Cholinergic agonists inhibit HMGB1 release and improve survival in experimental sepsiis", Nature Medicine, vol. 10, Nov. 2004, pp. 1216-1221.
Marty, et al., "Effects of Nicotine on b-Endorphin, aMSH, and ACTH Secretion by Isolated Perfused Mouse Brains and Pituitary Glands, In Vitro", Pharmacology Biochemistry & Behavior, vol. 22, pp. 317-325, 1985, pp. 317-325.

(Continued)

*Primary Examiner* — Leslie A. Royds Draper
(74) *Attorney, Agent, or Firm* — Panitch Schwarze Belisario & Nadel LLP

(57) ABSTRACT

Methods of treating renal failure are described. In particular, methods of treating renal failure by administration of pharmaceutical composition including a mixture of nicotine and salicylic acid are described.

1 Claim, No Drawings

(56) References Cited

OTHER PUBLICATIONS

Hedin, et al., "In vitro activation of amphibian dermal melanocytes by nicotine", Scand J. Dent. Res. 1986; 94: 57-65.
Glennon, "Nicotine and Pain", Med. Chem, Res. 13:1/2 (2004) 74-77.
Garnier, et al., "Functional characterization of a nonclassical nicotine receptor associated with inositolphospholipid breakdown and mobilization of intracellular calcium pools", Proc. Natl. Acad. Sci. USA, vol. 91, pp. 11743-11747, Nov. 1994.
Conte-Devolx, et al., "Effect of nicotine on in vivo secretion of melanocorticotropic hormones in the rat", Life Sciences, vol. 28, pp. 1067-1073; 1981 Pergamon Press Ltd.
Lamacz, M., et al., "Acetylcholine stimulates alpha-melanocyte-stimulating hormone release from frog pituitary melanotrophs through activiation of muscarinic and nicotinic receptors", Endocrinology, Aug. 1989; 125(2):707-14 (Abstract Only).
Louiset, et al., "Effect of acetylcholine on the electrical and secretory activities of frog pituitary melanotrophs", Brain Res. Nov. 19, 1990;553(2):300-8 (Abstract Only).
Bellinger, et al., "Effect of i.c.v. infusion of the alpha-MSH agonist MTII on meal patterns in male rats following nicotine withdrawal", Life Sci. Aug. 22, 2003;73(14):1861-72 (Abstract Only).
Hukkanen et al, "Metabolism and Disposition Kinetics of Nicotine," Pharmacological Reviews, vol. 57, No. 1, pp. 79-115 (2005).
Catania et al, "Alpha-Melanocyte-stimulating Hormone in Normal Human Physiology and Disease States," Trends in Endocrinology & Metabolism, vol. 11, No. 8, pp. 304-308 (2000).
Herrera, "Melanin: Fuel of the future?" Molecular Cell Biology, last accessed Sep. 14, 2011 at http://www.energiaadebate.com/Articulos/noviembre2007/imagenesnov/Solis.pdf (2007).
Serban et al, "Light induced production of hydrogen from water by catalysis with ruthenium melanoidins," International Journal of Hydrogen Energy, vol. 25, pp. 733-737 (2000).
Goodman et al, "Melanin directly converts light for vertebrate metabolic use: Heuristic thoughts on birds, Icarus and dark human skin," Medical Hypotheses, vol. 71, pp. 190-202 (2008).
Aliev et al, "Human photosynthesis, the ultimate answer to the long term mystery of Kleiber's law or E=M3/4: Implication in the context of gerontology and neurodegenerative diseases," Open Journal of Psychiatry, vol. 3, pp. 408-421 (2013).
Solis Herrera et al, "Human Photosynthesis and Central Nervous System's Diseases," Journal of Neurological Sciences (Turkish), vol. 29, No. 3, pp. 654-668 (2012).
Solis-Herrera et al, "The Pharmacological Modulation of Human Photosynthesis: A Real Hope for Bhopal, India," Journal of Research in Environmental Science and Toxicology, vol. 2, No. 7, pp. 136-146 (Aug. 2013).
Ulloa et al, "The 'cytokine profile': a code for sepsis," TRENDS in Molecular Medicine, vol. 11, No. 2, pp. 56-63 (Feb. 2005).
Steiner et al, "Nicotine administration and withdrawal affect survival in systemic inflammation models," J. Appl. Physiol., vol. 105, pp. 1028-1034 (2008).
Chiao et al, "Alpha-Melanocyte-stimulating Hormone Protects Against Renal Injury after Ischemia in Mice and Rats," J. Clin. Invest., vol. 99, No. 6, pp. 1165-1172 (Mar. 1997).
Park et al, "Inhibiting the Complement System Does Not Reduce Injury in Renal Ischemia Reperfusion," J. Am. Soc. Nephrol., vol. 12, pp. 1383-1390 (2001).
Chiao et al, "Alpha-Melanocyte-stimulating hormone inhibits renal injury in the absence of neutrophils," Kidney International, vol. 54, pp. 765-774 (1998).
Turkoglu et al, "Effects of alpha-MSH on ischemia/reperfusion injury in the rat sciatic nerve," Surg. Neurol. Int., vol. 3, No. 74 (Jul. 14, 2012).
Molander et al, "Pharmacokinetics of nicotine in kidney failure," Clin. Pharmacol. Ther., vol. 68, No. 3, pp. 250-260 (Sep. 2000) (abstract only).
Halimi et al, "Renal effects of smoking: potential mechanisms and perspectives," Nephrol Dial Transplant, vol. 15, pp. 938-940 (2000).
Sadis et al, "Nicotine Protects Kidney from Renal Ischemia/Reperfusion Injury through the Cholinergic Anti-Inflammatory Pathway," PLoS ONE, vol. 2, No. 5, p. e469 (2007).
Agarwal et al, "Oral; nicotine reduces proteinuria in spontaneously proteinuric rats," Abstracts of the Najaarssymposium, 85th meeting of the Dutch Federation of Nephrology (2009) (abstract only).
Pinsky (Contrib Nephrol, vol. 132, abstract; 2001 ).
Marty et al. (Pharmacology Biochemistry & Behavior, vol. 22, pp. 317-325; 1985).
Scholzen et al. (Endocrinology, vol. 144, No. 1, pp. 360-370; 2003).
Visser et al. (J Dev Physiol., vol. 1, No. 2, abstract; Apr. 1979).
Khan et al., "Management of Traumatic Hyphema with Raised Intraocular Pressure," Pak J Opthalmol, vol. 23, No. 4, pp. 217-220 (2007).
Vriese, "Prevention and Treatment of Acute Renal Failure in Sepsis," J Am Soc Nephrol, vol. 14, pp. 792-805 (2003).
Luksza et al., "Traumatic hyphema caused by eye injuries," Klin Oczna, vol. 107, Nos. 4-6, pp. 250-251 (2005) (Abstract only).
Dana et al., "Spontaneous and Traumatic Vitreous Hemorrhage," Opthalmology, vol. 100, No. 9, pp. 1377-1383 (1993) (Abstract only).
Zargarli et al., "Inhibition of Lipid Peroxidation by Antioxidants in the Vitreous Body During Hemorrhage," Bulletin of Experimental Biology and Medicine, vol. 106, No. 3, pp. 1253-1255 (1988).
Benowitz, N., "Pharmacology of Nicotine: Addiction and Therapeutics," Annu. Rev. Pharmacol. Toxicol., vol. 36, pp. 597-613 (1996).
Lamacz et al. "Nicotine-induced stimulation of alpha-MSH release in frog pituitary melanotrophs is mediated through a novel type of receptor," Annals of the New York Academy of Sciences, vol. 680, p. 520-523 (1993).
Solis Herrera et al., "The pharmacologic intensification of the water dissociation process, or human photosynthesis and its effect over the recovery mechanisms in tissues affected by bloodshed of diverse etiology," Int Jour of Clinical Medicine, vol. 2, pp. 332-338 (2011).
Rajora et al., "Alpha-MSH modulates local and circulating tumor necrosis factor-alpha in experimental brain inflammation," The Journal of Neuroscience, vol. 17, No. 6, pp. 2181-2186 (1997).
Shytle et al., "Cholinergic modulation of microglial activation by alpha7 nicotinic receptors," Journal of Neurochemistry, vol. 89, pp. 337-343 (2004).
Pavia et al., "Antimicrobial activity of nicotine against a spectrum of bacterial and fungal pathogens", J. Med. Microbiol., vol. 49, No. 7, pp. 675-676 (Jan. 7, 2000).
Han et al., "Antinociceptive Effect of Nicotine in Various Pain Models in the Mouse," Archives of Pharmacal Research, vol. 28, No. 2, pp. 209-215 (2005).
Solis Herrera et al., "The unexpected capacity of melanin to dissociate the water molecule fills the gap between the life before and after ATP," Biomedical Research, vol. 21, No. 2, pp. 224-226 (2010).
Shirname-More, "Smokeless tobacco extracts mutate human cells," Carcinogenesis, vol. 12, No. 5, pp. 927-930 (1991) (abstract only).
Yokode et al., "Cholesteryl ester accumulation in macrophages incubated with low density lipoprotein pretreated with cigarette smoke extract," Proc. Natl. Acad. Sci., vol. 85, pp. 2344-2348 (1988).
Thomas et al, "Mechaisms of Disease: nicotine—a review of its actions in the context of gastrointestinal disease," Nature Publishing Group, vol. 2, No. 11, pp. 536-544 (2005).
Yerger et al, "Melanin and nicotine: A review of the literature" Nicotine & Tobacco Research, vol. 8, No. 4, pp. 487-498 (2006).
Maximova et al, "Comparative evaluation of magnet-laser stimulation effect on lipid peroxidation processes in the aqueous humor in hyphema," SPIE, vol. 2673, pp. 214-217 (1996).
Santra et al, "Oxidative stress in gastric mucosa in Helicobacter pylori infection," Indian Society of Gastroenterology, vol. 19, pp. 21-23 (2000).
Pereira Filho et al, "Effect of N-acetylcysteine on vasospasm in subarachnoid hemorrhage," Arc Neuropsiquiatr, vol. 66, No. 6, pp. 918-922 (2010).

(56) References Cited

OTHER PUBLICATIONS

Sakaki et al, "Biological Defence Mechanism in the Pathogenesis of Prolonged Cerebral Vasospasm in the Patients with Ruptured Intracranial Aneurysms," Stroke, vol. 17, No. 2, pp. 196-202 (1986).
Deng et al., "Burprenorphine Given After Surgery Does Not Alter Renal Ischemia/Reperfusion Injury", American Association for Lab Animal Science, vol. 50, No. 6, pp. 628-632 (Dec. 2000).

* cited by examiner

METHODS OF USING QIAPINE

CROSS-REFERENCE TO RELATED APPLICATIONS

This application is a Divisional of U.S. application Ser. No. 14/531,538, filed Nov. 3, 2014, now U.S. Pat. No. 9,668,969, issued Jun. 6, 2017, which is a Divisional of U.S. application Ser. No. 13/401,892 filed Feb. 22, 2012, now abandoned, and the disclosures of which are incorporated herein by reference.

BACKGROUND OF THE INVENTION

Mammalian photosynthesis, the astonishing capacity of a mammalian body to use water as a source of electrons by means of its dissociation and subsequent reformation, is a discovery that is boiling up gradually as more and more people begin to understand the concept. The dogma that glucose is the source of energy will fade sooner or later. Glucose is only a source of biomass, important, but not the source of energy.

The intrinsic property of melanin to split and reform a water molecule was finally unraveled by our team in February 2002, after 12 years of study on the three main causes of blindness. See, e.g., WO2006/132521 and PCT/MX2006/000031. The interaction between matter (e.g., human retina) and radiated energy was part of the study. The understanding of the hitherto unsuspected capacity of melanin to absorb photonic energy and ultimately transform it into chemical energy was reached through the observation and simultaneous spectroscopy of the retina of about 6000 live patients that were carefully registered by digital means and analyzed by mathematical models, parametric and non-parametric depending of the dispersion data. After multiple efforts, we could finally understand this amazing capacity of melanin, and the hitherto unknown chlorophyll—like capacity of melanin as the origin of life. We could begin to rank the entire constituents of chemical reactions of a mammalian body that emerged gradually along 4 billion years of evolution, and believe that the number 1 reaction corresponds to the water splitting and reformation activity of melanin.

The reason is quite simple: eons of years of evolution has hinged on in this unique energy-releasing process that can be written as: $2H_2O \leftrightarrow 2H_2+O_2$. The subsequent biochemical reactions were slowly added during evolution until finally the first prokaryotic cell and thereafter eukaryotic cell emerged. Species evolution is a natural result of the ever changing chemical components implicated. Perhaps the component next to the origin of life was glucose, a compound that is widely spread over the earth and practically exists in any living thing. Glucose derivates, such as glycans, gained much attention in the last two decades in the biochemical world due to their highly complex roles as metabolic intermediates. Glycans are present in almost every place of the cell, such as cell membrane, the mitochondria, the Golgi apparatus, nucleus, etc. For example, cell membrane is heavily decorated with glycans, whose compositions are mainly unknown because of the complexity to characterize the sequences and structures of the sugars contained in each of them.

We have discovered the unsuspected capacity of melanin to split and reform a water molecule while releasing alternate but non-symmetric waves of energy, one of which is composed of diatomic hydrogen and the other one is composed of reformed water and high energy electrons. The cloud of doubts about the origin of life and the complexity of life itself has been changed dramatically by our discovery. We now know the origin of life on one hand and the present time on the other. At least the cloud of mystery had a beginning: energy.

The complexity of chemical processes that shape living things today is quite different after the occurrence and evolution of a highly complex series of biochemical reactions in 4 billion years. The beginning of life was relatively simple: every single reaction hinged on an apparently simple or straightforward source of energy. The complexity of life remains, but in a very different manner. We believe that the complexity of life began to form and evolve after the release of chemical energy by melanin during the 4 billion years of evolution.

The intrinsic property of melanin to split and reform a water molecule did not require the kind of evolution as that required for the subsequent life. The hitherto unsuspected capacity of melanin to split the water molecule has always existed with melanin. The evolution with melanin as the origin of life could exist, perhaps, in several parts of the universe. As time elapsed, the appropriate conditions were united, and then life occurred with her multiple ways of expression. The appropriate conditions include, for example, the temperature required for the presence of liquid water, a critical element. Melanin may exist in the extreme conditions of the space. In the order of abundance in the universe, we believe that the generation of life requires three elements: electromagnetic radiations or visible and invisible light, melanin and water.

The origin of life is a very controversial issue since ancient time. It mainly has been explained by means of theological stories. Some schools of thought propounded that after some abiotic processes, life did not begin until after the ATPase was created, thereafter ATP emerged, which supposedly served as the universal energy currency, then the evolution of life could take place. Others have tried to show that other types of molecules, such as protein or glucose, could be the real first step of life.

On the other hand, chlorophyll, despite its very important capacity to split a water molecule and produce energy required by a chemical reaction, cannot meet the requirement as the origin of life. This is because once the chlorophyll molecule is extracted from the plant leaf, seconds later, it irreversibly loses its main capacity to split the water molecule. Life occurred before chlorophyll, because chlorophyll must be inside of a living thing to perform its function.

Instead, melanin is the origin of life indeed, due to its extraordinary capacity to split and reform the water molecule, and that it can do so both inside and outside of a living thing, such as a cell. This water splitting and reformation capacity of melanin is intrinsic and is present in any place where the necessary conditions are fulfilled. Such conditions include the presence of light, visible and invisible; water in liquid (or even solid) state; and the presence of melanin itself. The water dissociation and reformation occur with the consequential release of energy, which is a unique and special kind of energy that best transforms photonic energy into chemical energy and is susceptible to uses by living things. Thus, melanin, as an operator or modulator of the natural positive or negative spikes of energy, absorbs the photonic energy and subsequently releases the resultant energy in significantly attenuated form that is brought to physiological levels. The narrow range of physiological parameters in which life is possible is determined by the structure-activity of melanin.

The ability of melanin to harvest the photonic energy of light and use the energy to split a water molecule and release energy readily utilizable by chemical reactions within a cell is critically important to the cell physiology, thus mammalian health, because energy is needed for all such chemical reactions in the body. There is a need for compositions and methods that enhance such water splitting and energy releasing activity within mammalian cells.

BRIEF SUMMARY OF THE INVENTION

It is now discovered that a mixture of compound A ((3-[(2S)-1-Methyl-2-pyrrolidinyl]pyridine) and compound B (phenol-2-carboxylate) functions as an enhancer of mammalian photosynthesis, and is effective to treat a variety of diseases or conditions in a subject.

In one general aspect, embodiments of the present invention relate to a method of enhancing mammalian photosynthesis in a subject, comprising administering to the subject an effective amount of a mixture of compound A and compound B:

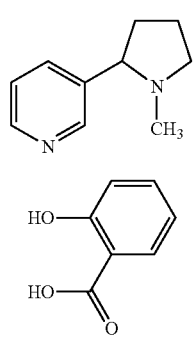

Compound A

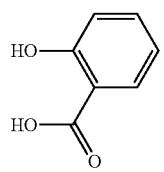

Compound B or an isomer, ester, prodrug, or pharmaceutically acceptable salt thereof.

Another general aspect of the present invention relates to a method of prophylactically and/or therapeutically treating a pathological condition in a subject in need of the treatment. The method comprises administering to the subject an effective amount of a pharmaceutical composition comprising a pharmaceutically acceptable carrier and a mixture of compound A and compound B, or an isomer, ester, prodrug, or pharmaceutically acceptable salt thereof, thereby prophylactically and/or therapeutically treating the pathological condition in the subject.

Yet another general aspect of the present invention relates to a pharmaceutical composition comprising a pharmaceutically acceptable carrier and a mixture of compound A and compound B, or an isomer, ester, prodrug, or pharmaceutically acceptable salt thereof, as well as a method of preparing the pharmaceutical composition.

Other aspects, features and advantages of the invention will be apparent from the following disclosure, including the detailed description of the invention and its preferred embodiments and the appended claims.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, "mammalian photosynthesis" refers to a process conducted by melanin in a mammalian cell where water is used as a source of electrons by means of its dissociation and reformation and photonic energy is absorbed and converted into a form of energy that is readily utilizable by the cell. Mammalian photosynthesis is a highly complex process unsuspected so far. It could be represented by the biochemical equation: $2H_2O \leftrightarrow 2H_2 + O_2$.

As used herein, "QIAPINE™" refers to a mixture of compound A and compound B

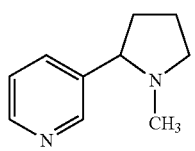

Compound A

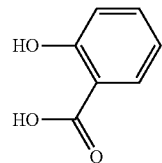

Compound B in any possible isomeric form (e.g., optical isomer, enantiomer, diastereomer, racemate or racemic mixture), ester, prodrug, metabolite form, or pharmaceutically acceptable salt thereof. QIAPINE™ was developed as an enhancer of mammalian photosynthesis.

QIAPINE™ includes a mixture of compound A and compound B, or an isomer, ester, prodrug, or pharmaceutically acceptable salt thereof, mixed at any ratio.

According to embodiments of the present application, QIAPINE™ comprises compound A and compound B mixed at a ratio of about 1:10, 1:8, 1:6, 1:4, 1:2, 1:1, 1.5:1, 2:1, 4:1, 6:1, 8:1 or 10:1, by weight.

The phrase "pharmaceutically acceptable salt(s)", as used herein, means those salts of a compound of interest that are safe and effective for use in mammals and that possess the desired biological activity. Pharmaceutically acceptable salts include salts of acidic or basic groups present in the specified compounds.

As used herein, the term "subject" means any animal, preferably a mammal, most preferably a human, to whom will be or has been administered compounds or compositions according to embodiments of the invention. The term "mammal" as used herein, encompasses any mammal.

Examples of mammals include, but are not limited to, cows, horses, sheep, pigs, cats, dogs, mice, rats, rabbits, guinea pigs, monkeys, humans etc., more preferably, a human. Preferably, a subject is in need of or has been the object of observation or experiment of, treatment or prevention of a pathologic condition.

As used herein, "an effective amount" refers to the amount of QIAPINE™ or a pharmaceutical composition comprising QIAPINE™ that elicits the biological or medicinal response in a tissue system, animal or human that is being sought by a researcher, veterinarian, medical doctor or other clinician, which includes prevention or alleviation of the symptoms of the disease or disorder being treated. In a preferred embodiment, the effective amount of a pharmaceutical composition comprising QIAPINE™ is effective to treat, improve the treatment of, or prophylactically prevent the disease or disorder associated with defective or insufficient mammalian photosynthesis.

One skilled in the art will recognize that the effective amount to be used in the instant invention can vary with factors, such as the particular subject, e.g., age, diet, health, etc., severity and complications and types of the diseases or disorders sought to be treated or prevented, the formulation used, etc. In view of the present disclosure, standard procedures can be performed to evaluate the effect of the administration of a composition to a subject, thus allowing a skilled artisan to determine the effective amount.

QIAPINE™ was used for prophylactical and/or therapeutical treatment of a variety of diseases or conditions, see, e.g., Example 2 below. The results were very encouraging and overwhelming.

Without wishing to be bound by theory, we began to understand gradually that the enhancement of the energy released by mammalian photosynthesis via melanin is of prime importance to the health of the mammalian body. When the energy levels are adequate, our body goes into equilibrium and functions properly. After about 4 billion years of evolution, our body is quasi-perfect, and only needs optimal levels of photosynthesis or water dissociation and reformation. We believe that, as the origin of life, melanin affects each of the biochemical reactions occurring in our cells. These reactions depend completely on the energy resulting from mammalian photosynthesis in order to function adequately.

After years of continued work and thousands of patients treated, we now believe that any disease, whatever it could be, is associated with a malfunction of mammalian photosynthesis, such as reduced production of the resultant energy. In the presence of low levels of diatomic hydrogen and electrons of high energy, the cell could die immediately, e.g., in seconds, or the entire organism could go into imbalance. The signs and symptoms that, could be attributed to any particular disease are just manifestations of the imbalance between the available energy and the requirements of it by the biomass. Recall glucose is a source of biomass and water is a source of energy, in addition to the other roles described for both compounds. The balanced relationship between the matter and the energy are reestablished when the subject recovers and the disease is cured. The balanced relationship only occurs in a narrow range where the expression of life can occur adequately.

In addition, the mammalian photosynthesis can be turned down by various factors or conditions, such as cold weather (as in plants), iron supplements, hormonal imbalance such as female hormones, alcohol consumption, antidepressants, pesticides, herbicides, adverse or side effects of medicaments, anesthesia agents, contaminated water, etc. Thus, enhanced mammalian photosynthesis can also be used to counteract the frequent presence of any of these factors or conditions.

QIAPINE™ induces or enhances mammalian photosynthesis, a primary process of life, in which the harvesting of the universal nutrient, i.e., sunlight, is achieved by cells of our body. The water dissociation and reformation by melanin is a robust process, every cell of a mammalian body has the necessary machinery to perform the function. However, the concert among cells in a mammalian body, e.g., estimated 100 trillion cells on average in a human body, which makes better and efficient use of the chemical energy in a systemic manner, is where the complexity of our body is manifested and where QIAPINE™ works.

QIAPINE™ enhances mammalian photosynthesis by binding to different types of receptors localized in the cell membrane of practically every single cell. The enhancement of the mammalian photosynthesis in mammalian body has a profound effect in practically every aspect of a mammalian body. Because every single reaction of the approx. 30 000 (estimated number) reactions that happen simultaneously every minute in a mammalian body needs energy along the entire reaction, from the beginning to the end. It's not necessary to describe the various metabolic pathways in exhaustive terms for the present invention. Rather, it is sufficient to say that the starting point is when enough energy levels from photosynthesis are available, then the highly intricate biochemical reactions that life requires could adequately happen.

QIAPINE™ induces the release of the chemical energy in a highly ordered manner, i.e., in a physiologic form. That's the reason why uses of this composition have a very low incidence and prevalence of secondary effects. Patient gets huge benefits, due to the wide effect of the released energy. The impact of this released energy is not merely punctual or isolated in anyway, it is fully generalized instead. Therefore, QIAPINE™ significantly improves the overall body functions, which in turn prophylactically and/or therapeutically treats any illness of the body, including even the mental diseases.

Examples of diseases or disorders that can be treated by QIAPINE™ include, but are not limited to, chronic and/or acute inflammatory diseases, degenerative diseases, such as Huntington's disease, infectious diseases, central nerve system diseases, proliferative diseases, such as tumors or cancers, metabolic diseases, such as diabetes, cardiovascular diseases, collagen related diseases, immune or autoimmune diseases, etc.

The methods according to embodiments of the present invention can optionally comprise administering to the subject other therapeutically active ingredients or treatments that work synergistically or additively with QIAPINE™.

Whether administered alone or in combination with an additional therapeutic agent, QIAPINE™ can be administered by any known route of administration, including, but not limited to, orally, sublingually, buccally, topically, parenterally (including subcutaneous, intravenous, intramuscular, and intrasternal injection or infusion administration techniques), by inhalation spray or rectally in dosage units or pharmaceutical compositions containing conventional pharmaceutically acceptable carriers. Any such dosage units or pharmaceutical compositions are within the scope, of the present invention. Any of these dosage forms may be prepared according to any method or compounding technique known in the art for the manufacture of pharmaceutical compositions in view of the present disclosure.

The amount of therapeutically active ingredients to be included in a dosage form will depend upon the patient being treated, the mode of administration and the desired delivered dose. Representative pharmaceutical compositions will generally include from about 0.01 mg to about 1000 mg, from about 0.1 mg to 500 mg, from about 0.1 mg to about 100 mg, or from about 1 mg to about 50 mg, of QIAPINE™.

In an embodiment of the present invention, QIAPINE™ is administered sublingually at about 1 mg/ml to 4 mg/ml, preferably 3 mg/ml, in aqueous vehicle.

According to an embodiment of the present invention, QIAPINE™ is administered sublingually at about 0.000050 g/kg/day to about 0.00015 g/kg/day, such as at about 0.000050 g/kg/day, 0.000075 g/kg/day, 0.000100 g/kg/day, 0.000125 g/kg/day, or 0.000150 g/kg/day.

The frequency of the administration varies depending on the condition of the subject being treated. It can be hourly, every few hours or even daily.

According to an embodiment of the present invention, QIAPINE™ is sublingually administered three drops (at about 1 mg/ml to 4 mg/ml) hourly upon initial treatment. After the subject's condition is stabilized and improved enough, QIAPINE™ can be administered every two to three hours during the day for weeks or months until recovery.

This invention will be better understood by reference to the non-limiting example that follows, but those skilled in the art will readily appreciate that the example is only illustrative of the invention as described more fully in the claims which follow thereafter.

EXAMPLE 1

Synthesis of QIAPINE™

QIAPINE™, a mixture of two compounds: A ((3-[(2S)-1-Methyl-2-pyrrolidinyl]pyridine) and B (phenol-2-carboxylate), or an isomer, ester, prodrug, or pharmaceutically acceptable salt thereof, can be synthesized using methods known to those skilled in the art in view of the present disclosure. Each of compounds A and B, or an isomer, ester, prodrug, or pharmaceutically acceptable salt thereof is prepared individually and then mixed together.

For example, compound A ((3-[(2S)-1-methyl-2-pyrrolidinyl]pyridine)) was prepared by first performing a halogen-lithium exchange of 3-bromopyridine with n-BuLi, followed by treatment with the lactone to obtain a hydroxyketone. The hydroxyketone was oxidized to the corresponding aldehyde via the Swerm oxidation method (using oxalyl chloride, DMSO, and $Et_3N$ as an organic base). Subsequently, (pyridine-3'-yl)-4-oxobutanone was reacted with 2,3,4,5-tetra-O-pivaloyl-β-D-galactopyranosylamine. A final acidic hydrolysis (using 1M HCl in methanol) yielded 3-(2-pyrrolidinyl)pyridine, and alkylation with EtOCOCl (1.2 equiv.), $Et_3N$ (1.3 equiv.) in diethylether followed by $LiAlH_4$ (1.2 equiv. in THF) at 0° C. affords 3-[(2S)-1-methyl-2-pyrrolidinyl]pyridine.

Compound B (phenol-2-carboxylate) was prepared by treating sodium with carbon dioxide at high pressure (100 atm) and high temperature (390 K). Acidification of the product with sulfuric acid yields phenol-2-carboxylate.

Finally, compounds A and B were mixed in proportion of 2.6 ml (A) with 1.8 mg (B) to yield the final product, QIAPINE™.

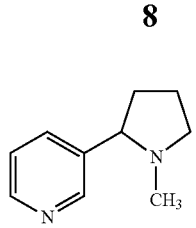

Compound A

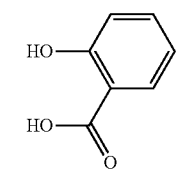

Compound B

Chemical Formula: $C_{17}H_{20}N_2O_3$
Exact Mass: 300.15
Molecular Weight: 300.35
m/z: 300.15 (100.00%), 301.15 (18.7%), 302.15 (2.4%)
Elemental Analysis: C, 67.98; H, 6.71; N, 933; O, 15.98

EXAMPLE 2

Treatments with QIAPINE™ a.) Male patient, 4 year old, broken down by a car, in persistent vegetative state (coma), Glasgow level 2, one month of evolution, with tracheotomy and gastrostomy. MRI studies found chronic subdural hematoma, diffuse axonal damage, and changes in size and form of ventricles and subarachnoid space. QIAPINE™ administration was started at a dose of three drops (3 mg/ml in aqueous solution) sublingually every hour, in addition to the treatments by Epamin and Ampiciline for lung manifestations. The clinical response was amazing. Twelve hours after the initial administration of QIAPINE™, the patient was awake. Thereafter, the clinical evolution was astonishing. Three days later tracheotomy tube was not necessary and was removed, one week later gastrostomy feed tube was also removed. Slowly the patient began to walk, with some degree of spasticity which faded gradually. Presently the recovery level was around of 80-90%.

b.) Female patient, 18 month old, was found floating in a swimming pool. Admitted to an emergency room of the local hospital with diagnosis of asphyxia by immersion. At physical exploration, her pupils were dilated, but she still had irregular heartbeats. Resuscitation maneuvers were applied and QIAPINE™ was administered at a dose of three drops (3 mg/ml in aqueous solution) sublingually every hour. Three days later the patient was discharged practically with no neurological sequels. After discharging, QIAPINE™ was administered every two hours during the day for several more weeks.

c.) Male patient, 43 year old, with painful erections in 4 months, both in early morning and during night, with a duration time between 2 and 4 hours. The diagnosis was priapism of low flow type. QIAPINE™ was administered at a dose of three drops (3 mg/ml in aqueous solution) under the tongue every two hours during the day. Six weeks later, the improvement reached 80-90%.

d.) Male patient, 20 year old, otherwise healthy, but had suffered traumatic hyphema caused by a blunt contusion in the left eye 10 days prior, with immediate vision loss and hard pain. During the first ten days, the patient was treated with steroids and maximal therapy to lower the intraocular pressure, with no apparent success, e.g., having bloodshed that filled the anterior chamber of the eye and an intraocular pressure (IOP) of 40 mmHg. While evaluating the surgical option, the patient came to our office. We recommended him a treatment to enhance the mammalian photosynthesis. The patient and his family accepted our recommendation. QIAPINE™ was administered at a dosage of three drops (3 mg/ml in aqueous solution) sublingually each hour. The therapeutic result was amazing. Five weeks later, vision was recovered 20/25 with an IOP of 16 mmHg. Thereafter, QIAPINE™ was administered every two hours during the day for several more weeks.

e.) Male patient, 21 year old, otherwise healthy, but had suffered traumatic hyphema caused by blunt contusion in the right eye one week prior, followed by pain and vision loss. The patient was treated elsewhere with bed rest, steroids and maximal therapy in an attempt to lower intraocular pressure, with no apparent success, e.g., having bloodshed that filled the anterior chamber of the eye and an intraocular pressure (IOP) of 40 mmHg. When the surgical option seemed like the only option to avoid corneal complications, the patient came to Our office. After examination, we offered the patient treatment based on mammalian photosynthesis enhancement. The patient and his family accepted our recommendation. QIAPINE™ was administered at a dosage of three drops (3 mg/ml in aqueous solution) sublingually each hour. Results were extraordinary. Five weeks later, vision was recovered 20/25 with an IOP of 16 mmHg Thereafter, QIAPINE™ was administered every two hours during the day for several more weeks.

f.) Female patient, 64 year old, having type 2 diabetes since 1992, and systemic arterial hypertension since 1987. The patient came to see us due to sudden loss of vision in the right eye. At examination, bloodshed in the vitreous of the right eye was found. IOP was 20 mm Hg in both eyes. The patient was treated only with mammalian photosynthesis enhancement by sublingual administration of QIAPINE™ at dosages of three drops (3 mg/ml in aqueous solution) each hour during the day. Three months later, vitreous hemorrhage in her eye disappeared and vision recovered. Thereafter, QIAPINE™ was administered every two hours during the day.

g.) Male patient, 38 year old, having 18 years of type 1 diabetes, and 10 years of systemic arterial hypertension. About six months prior to his initial visit to our office, the patient had an abrupt loss of vision of the left eye by vitreous hemorrhage and was treated elsewhere with laser without success. The patient actually came to our office for examination due to sudden vision loss in his right eye 3 or 4 days prior to his initial visit. The ocular fundus showed vitreous hemorrhage that covered the macular area, and therefore the central vision was severely impaired. Treatment based on the enhancement of mammalian photosynthesis was initiated at a dosage of 3 drops (3 mg/ml in aqueous solution) of QIAPINE™ administered sublingually each hour during the day. Seven days later, examination showed significant absorption of the bloodshed, and the macula recovered its function. After anatomical recovery was reached several weeks later, QIAPINE™ was administered every two hours during the day.

h.) Female patient, 64 year old, with antecedents of ischemic cardiopathy 2 years prior, with dyslipidemia, dizziness, insomnia; dyspnea on effort, with sudden loss of consciousness a few hours prior. The clinical diagnosis was vascular cerebral event that affected the left cerebral parenchyma at basal ganglia level and subarachnoid hemorrhage in Sylvian Area, on the left side. While the patient was at the ER, due to several circumstances and because the family gave their approval, the mammalian photosynthesis enhancer QIAPINE™ was administered at a dosage of three drops (3 mg/ml in aqueous solution) sublingually each hour, without stopping other common support measures. Six hours later, clinical symptoms had improved dramatically. From the CAT scan, hemorrhage diminished about 50%. Thereafter the patient continued with the QIAPINE™ treatment and was discharged with no surgery 5 days later, without neurological sequels. After symptoms disappeared about three months later, QIAPINE™ was administered every two hours during the day.

i.) Child, 5 year old, male, was knocked down by a car on Sep. 26, 2010, with loss of consciousness and coma. At the first emergency room visit, the coma was classified as Glasgow 2. The doctors intubated him for 7 days. Mainly due to the poor prognosis, the patient was taken to our hospital on Oct. 6, 2010, where an CT Scan was done, and chronic bilateral subdural hematomas was diagnosed. After the patient was moved to our hospital, QIAPINE™ was initiated at once during the first day of hospitalization, at a dosage of three drops (3 mg/ml in aqueous solution) sublingually every hour and the response of the patient was dramatic. On the second day of hospitalization the Glasgow level was at 15. Thereafter, QIAPINE™ was administered every two hours during the day, the improvement continued and neurological recovery reached 90-95%.

j.) Female, 81 years old, with Alzheimer's disease diagnosed in 2007. In spite of several treatments with acetyl cholinesterase inhibitors the clinical picture was worsening. Treatment with QIAPINE™ at a dose of three drops (3 mg/ml in aqueous solution) sublingually every two hours during the day was started in January 2010. Six weeks later the improvement in attention, memory, and psychomotor speed was significant. Significant improvements in patient/informant ratings of cognitive impairment were also observed, QIAPINE™ administration was continued every two hours during the day.

k.) Female patient, 61 years old, with diagnosis of Huntington's Disease since 2006. In spite the patient's receiving of traditional treatment during previous years, the illness worsened gradually and in the last two months a progressive involuntary tongue movements appeared. We started QIAPINE™ at doses of three drops (3 mg/ml in aqueous solution) each hour during the day, sublingually and all previous medications were suspended. Three weeks later, the improvement in the clinical picture was dramatic. For example, her tongue movements have disappeared. The phrase Huntington's Chorea is much more common in people of Western European descent than in those of Asian or African ancestry" is very well explained by the amount of melanin.

L.) Male patient with diabetic foot of three years of evolution, 68 years old, the ulceration comprised of two foot fingers that were excised surgically, but, the surgical wound could not be healed. The patient was treated with QIAPINE™ at doses of three drops (3 mg/ml in aqueous solution) sublingually each hour during the day and gradually the aspect of the entire foot and leg improves markedly. Six months later the ulcer of the foot was closed completely.

M.) Female patients, two siblings of 9 and 11 years old respectively. Since 10 months of age Ataxia Telangiectasia diagnosis was made in both. The older sister loss weight notably and even the possibility of gastrostomy was considered. At first examination both patients required to be helped by their parents to practice any activity, such as walking, bathroom, etc., and depression symptoms were constant. QIAPINE™ treatment was started at doses of three drops (3 mg/ml in aqueous solution) sublingually each hour during day. Three months later, the older sister increased 1 kg of weight monthly, in addition to the improvement in all other spheres of mind and body. The younger sister could walk alone, and the physical dependence for usual activities was diminished markedly. The improvement has been progressive. No other medication has been used.

N.) Male patient of 65 years old with back pain since 2003. Non-diabetic, without hypertension. In spite of multiple medical treatments, the clinical picture was worsen each time and surgical treatment was seen as only the option. Patient came to our office, and after examination, QIAPINE™ was started at doses of three drops (3 mg/ml in aqueous solution) every two hours during the day. One month later, the pain improved in 80-90%. No other medication was used and our treatment was advised to be used most of the time.

O.) Female patient, 14 years old, with diagnosis of primary renal failure with a renal function of 20% approximately. Alter examination, QIAPINE™ was started at doses of three drops (3 mg/ml in aqueous solution) each hour during the day. Four months later, renal function returned to 1009%. Treatment was maintained most of the time.

Epilepsy, Alzheimer, depression, attention deficit; systemic arterial hypertension, diabetes mellitus type 1 and 2, migraine, restless legs, fibromyalgia, asthma; pulmonary fibrosis, and several other disease have been treated with QIAPINE™ with very encouraging results.

Safety and tolerance of sublingual administration of QIAPINE™ were excellent.

Again, without wishing to be bound by theory, we believe that mammalian photosynthesis was turned down by a wide variety of diseases, conditions or injuries, such as coma, drowning, priapism, traumatic hypherna, diabetes, hypertension, ischemic cardiomyopathy, vitreous hemorrhage, dementia or Alzheimer's disease, etc., illustrated above. Because adequate energy level is basic to cellular metabolism, it is critical to maintain sufficient level of mammalian photosynthesis to procure a fast recovery of the anatomy and physiology of cells, tissues, organs and systems, thus recovery of the diseases, conditions or injuries. Eukaryotic cells are highly resistant if its photosynthesis or the water dissociation level is adequate.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method of treating renal failure in a human subject in need thereof, the method comprising sublingually administering to the subject an effective amount of an aqueous pharmaceutical composition comprising a pharmaceutically acceptable carrier and 3 mg/mL of a mixture of compound A, or a pharmaceutically acceptable salt thereof, and compound B, or a pharmaceutically acceptable salt thereof:

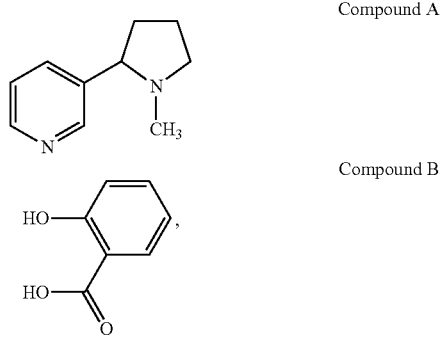

wherein the mixture comprises the compound A, or pharmaceutically acceptable salt thereof, and the compound B, or pharmaceutically acceptable salt thereof, at a ratio of about 1.5:1, and wherein the aqueous pharmaceutical composition is administered once per hour at a dose of 3 drops, thereby treating the renal failure in the subject.

* * * * *